United States Patent [19]

Eby, III

[11] Patent Number: 5,002,970

[45] Date of Patent: Mar. 26, 1991

[54] FLAVOR MASKED IONIZABLE ZINC COMPOSITIONS FOR ORAL ABSORPTION

[76] Inventor: George A. Eby, III, 2109 Paramount Ave., Austin, Tex. 78704

[21] Appl. No.: 182,983

[22] Filed: Apr. 18, 1988

Related U.S. Application Data

[63] Continuation-in-part of Ser. No. 102,750, Sep. 24, 1987, Pat. No. 4,956,385, which is a continuation of Ser. No. 667,097, Nov. 1, 1984, abandoned, which is a continuation-in-part of Ser. No. 667,097, May 14, 1982, Pat. No. 4,503,070, which is a continuation-in-part of Ser. No. 288,750, Jul. 31, 1981, abandoned, which is a continuation-in-part of Ser. No. 22,620, Jan. 5, 1981, abandoned.

[51] Int. Cl.$^5$ .................. A61K 9/14; A61K 9/20; A61K 31/315; A61K 33/30
[52] U.S. Cl. .................. 514/494; 514/974; 514/849; 514/888; 424/440; 424/441; 424/442; 424/439; 424/489; 424/464; 424/641; 424/643
[58] Field of Search .............. 424/464, 58, 439, 440, 424/441, 442, 489, 641, 643; 514/494, 974, 849, 888

[56] References Cited

U.S. PATENT DOCUMENTS

| | | | |
|---|---|---|---|
| 944,738 | 12/1909 | Loose et al. | 424/95 |
| 994,738 | 12/1909 | Loose | 424/95 |
| 1,488,097 | 3/1922 | Creger | 514/494 |
| 1,861,189 | 5/1932 | Pasternack | 424/55 |
| 2,527,686 | 10/1950 | Sandberg | 424/50 |
| 3,622,662 | 11/1971 | Roberts | 424/58 |
| 4,146,606 | 3/1979 | Yamaga | 424/52 |
| 4,367,218 | 1/1983 | Jacobson | 424/49 |
| 4,444,755 | 4/1984 | Horrobin | 424/145 |
| 4,469,674 | 9/1984 | Shah et al. | 424/52 |
| 4,684,528 | 8/1987 | Godfrey | 424/49 |

FOREIGN PATENT DOCUMENTS 3431727 3/1986 Fed. Rep. of Germany .
0240182 3/1969 U.S.S.R. .

OTHER PUBLICATIONS

Merck's 1901 Manual of the Materia Medica, pp. 124–125.
Merck's Manual of the Materia Medica, (1923), pp. 160–161.
Franklin, (1931), Brit. Med. Jrnl., Jun. 27, 1931, pp. 1115–1116.
Shields (1936), "The Ionization Treatment of Hay Fever", pp. 645–648.
Bailey, et al. (1937), Brit. Med. Jrnl., Apr. 17, 1937, p. 808.
Marone et al. (1980), Jrn. All. Clin. Immunology, 65:171.
Handbook of Non-Prescription Drugs, 6th Edition, p. 317.
The Pharmacological Basis of Therapeutics, 5th Edition, pp. 1000–1001.
Al-Nakib et al., "Prophylaxis and Treatment of Rhinovirus Colds with Zinc Gluconate Lozenges", Jrnl. Antimicrob. Chemother., 20(6):893–901, 1987.
Godfrey (1988), Antimicrob. Agents Chemother., 32:605.
Eby (1988), Antimicrob. Agents Chemother., 32:606.
Farr et al. (1988), Antimicrob. Agents Chemother., 32:607.
Martin (1988), Antimicrob. Agents Chemother., 32:608.
Farr et al. (1987), Antimicrob. Agents Chemother., 31:1183.
Al-Nakib et al. (1987), Jrnl. Antimicrob. Chemother., 20:893.
Pasternak (1987), Bioscience Rep., 7(2):81.
"Zinc Zaps Common Cold", The Evening Wellington, New Zealand; Aug. 10, 1987, p. 1.
Zerial et al. (1985), Antimicrob. Agents Chemother., 27(5):846.
"Zinc vs Colds" (1984), Austin American Statesman, Dec. 2, 1984, p. A15.
Eby et al. (1984), Antimierob. Agents Chemother., 25(1):20.
Couch (1984), Jrnl. Infect. Dis., 150(2):174.
Hayden et al. (1984), Jrnl. Infect. Dis., 150(2):174.
Samo et al. (1984), Jrnl. Infect. Dis., 150(2):181.
Phillpotts et al. (1983) Antimicrob. Agents Chemother., 23(5):671.
Anderson et al. (1983), "Viral Respiratory Illnesses", Medical Clinics of North America, 67(5):1009.
Levandowski et al. (1982), Antimicrob, Agents Chemother., 22(6):1004.
Andermann et al. (1982), Eur. Jrnl. Drug Metab. Pharma., 7(8):233.
Hayden et al. (1982), Antimicrob. Agents Chemother., 21(6):892.
"Idoxuridine and some other Antiviral Agents" (1982), Martindale, The Extra Pharmacopoeia, 28th Edition, pp. 820–827.
Giron (1982), Proc. Soc. Exp. Biol. Med., 170:25.
Korant (1979) "Inhibition of Viral Protein Cleavage", in Design of Inhibitor of Viral Functions, K. Gauri, ed., Academic Press.
Korant (1979), "Role of Cellular and Viral Proteases . . . " in The Molecular Biology of Picornoviruses, pp. 149–173.
Webster's New Collegiate Dictionary (1979), "lozenge" and troche.

(List continued on next page.)

Primary Examiner—Ronald W. Griffin

[57] ABSTRACT

An oral composition containing ionizable compounds of zinc flavor-masked with anethole and prepared in the forms of pleasant tasting lozenges, soft candies, syrups, powders and chewing gums for delivery of zinc to the oral and oral pharyngeal mucosa of a human with said composition being absent the taste or aftertaste of zinc, and being primarily intended for use in treating the common cold.

10 Claims, No Drawings

OTHER PUBLICATIONS

Korant et al. (1976), *Jrnl. Virol.*, 18(1):298.
Butterworth et al. (1976), *Arch. Virol.*, 51:109.
Harmon et al. (1976), *Proc. Soc. Exp. Biol. Med.*, 152:598.
Korant et al. (1974), *Nature*, 248:588.
1948 Quarterly Cumulative Index Medicus, vol. 44, p. 797.
Van Voris, "Antiviral Chemotherapy", Chapter 8 in *Textbook of Human Virology*, pp. 193–229.
Levandowski, "Rhinoviruses", Chapter 16 in *Textbook of Human Virology*, pp. 391–405.
Tyrrell et al., "Antirhinovirus Drugs" pp. 340–341.
Chapter 57, "Antiviral Chemotherapy & Prophylaxis," in Review of Medical Pharmacology, 7th Edition, Meyers et al. eds., pp. 589–592.
Akzo Chemie "Gluconates", pp. 5–15.
Unpublished letter of Mr. Eby's.
Eby et al., "Effect of Zinc Orotate Lozenges with Zinc Gluconate Nasal Spray in Common Cold Treatment—A Double Blind Study," unpublished.
*Modern Drug Encyclopedia and Therapeutic Guide*, Jacob Gutman, New York, 1941, Entry Zinc Borate.
*Hack's Chemical Dictionary*, 4th ed. McGraw—Hill Book Co., N.Y. 1969, p. 45.

FLAVOR MASKED IONIZABLE ZINC COMPOSITIONS FOR ORAL ABSORPTION

This application is a continuation-in-part of applicant's copending application U.S. Ser. No. 102,750, filed Sept. 24, 1987, now U.S. Pat. No. 4,856,385 which is a continuation of application Ser. No. 667,097, filed Nov. 1, 1984, now abandoned, which was a continuation-in-part application of U.S. Pat. No. 4,503,070, filed May 14, 1982, issued Mar. 5, 1985 which was a continuation-in-part application of U.S. Ser. No. 288,750, filed July 31, 1981, now abandoned, which was a continuation-in-part application of U.S. Ser. No. 22,620 filed Jan. 5, 1981, now abandoned.

FIELD OF INVENTION

This invention relates to a method for masking the flavor of compositions for oral absorption which contain ionizable zinc compounds. More particularly, this invention relates to compositions containing ionizable zinc compounds and anethole which, when applied to the oral and oral pharyngeal membranes are palatable and without undesirable aftertaste yet allow the oral absorption of zinc.

GENERAL BACKGROUND

The art of managing metallic ions in food products has received much attention by the food industry. Metallic ions of iron, copper and zinc can be present in some food products with adverse effects on food integrity. If they are allowed to remain in some food products even in low concentrations, such metallic ions can greatly reduce the shelf life of some fats, oils and other foods greatly reduce the shelf life of some fats, oils and other foods that are subject to spoiling and oxidization.

Sequestrants are chemicals that deactivate or stabilize these metallic ions by chemically tying up the metal ions through chemical reactions to form stable complexes that do not adversely affect the integrity or quality of such food products. Sequestrants are also known as sequestering agents, stabilizers, chelators, chelating agents and metal scavengers. Sequestrants help to establish, maintain, and enhance the integrity of many food products. From a food manufacturing viewpoint, sequestrants serve to stabilize or enhance the numerous properties identified with wholesome food including color, flavor and texture. Usually, sequestrants chemically react with metallic ions to form complexes which, depending on the stability of the metal complex, tend to alter the properties and effects of the metal in a substrate. Many sequestrants employed in food production occur naturally in nature. They include as monocarboxylic acids gluconic and acetic acids which weakly sequester zinc ions; as hydroxycarboxylic acids citric and tartaric acids which may sequester zinc ions; as amino acids such as sweet tasting lysine, glycine, leucine, alanine, and valine which may sequester zinc ions; and various macromolecules such as porphyins, peptides and proteins. Certain commercial sweeteners such as saccharin, sorbitol, mannitol and a constituent of aspartame, phenylalanine, have also been shown to bind with or sequester certain metals. For sequestration, chelation, to occur two general conditions must be met: (a) the ligand must have the proper steric and electronic configuration in relation to the metal ion being complexed and (b) the surrounding milieu (pH, ionic strength, solubility, etc) must likewise be conducive to complex formation. That sequestration of metal ions is a desirable goal of food manufacturers is well known in the art. Sequestration in food is reviewed and referenced in *CRC Handbook of Food Additives*, 2nd Ed. 1972. Stability constants are exhaustively compiled in *Stability Constants of Metal-Ion Complexes* and its supplement which are special publications 17 and 25 of The Chemical Society published by Burlington House, London in 1964 and 1968.

However, the desirability of sequestering metal ions in all cases must be challenged in view of the nature of some metal chelators relative to the environment in which their use is intended. For example, the use of zinc gluconate lozenges and similar means has been described as a method for reducing the duration of common cold symptoms (U.S. Pat. No. 4,503,070, Mar. 5, 1985 and any reissues and continuations-in-part). In such usage, zinc ions are only weakly bound by the gluconate moiety. Judging from the stability constant of zinc gluconate, log $K_1$ 1.70, nearly all zinc appears to be ionized in solution with water from saliva at any given time. Such ions appear available for those biochemical activities in the oral and oral pharyngeal mucous membranes that result in a reduction in the duration of common cold symptoms. Although the exact nature of the biochemical activity of zinc ions in reducing the duration of common cold symptoms remains to be determined, it appears that the zinc complex must be ionizable. Published articles, "Reduction in Duration of Common Cold Symptoms by Zinc Gluconate Lozenges in a Double Blind Study", *Antimicrobial Agents and Chemotherapy*, 1984, 25(1), pp20-24 by George A. Eby, et al; and "Prophylaxis and Treatment of Rhinovirus Colds with Zinc Gluconate Lozenges", *Journal of Antimicrobial Chemotherapy*, 1987, 20(6), pp 893-901 by W. Al-Nakib, et al, both use zinc gluconate with no additional metal sequestrants added and both showed a marked reduction in the duration of common cold symptoms.

Conversely, in a similar study "Two Randomized Controlled Trials of Zinc Gluconate Lozenge Therapy of Experimentally Induced Rhinovirus Colds", *Antimicrobial Agents and Chemotherapy*, 1987 31(8) pp 1183-1187, by Jack M. Gwaltney, Jr. et al, citric acid, a very strong zinc chelator, was used in the lozenges in large amounts which were sufficient to eliminate the taste of zinc, resulting in no reduction in the duration of the common cold. The stability constant of citric acid for zinc ions is generally accepted to be log $K_1$ 4.5. In oral use in lozenge form, zinc gluconate rapidly ionizes; as does zinc combined with other ligands having low stability constants. It is known in the art that if such occurs in the presence of sufficient amount of an acid having a high stability constants for zinc ions such as equimolar (or greater) citric acid, a new, vastly stronger equilibrium may occur. Such equilibrium may result in stable compounds having little or no bioavailabilty at normal pH as would be found in saliva. In the case of lozenges containing zinc gluconate with citric acid, soluble zinc complexes were shown to be tasteless and were proposed to be sufficiently biologically available to be effective in reducing the duration of common colds. However, with addition of sufficient citric acid, there occurs in saliva such powerful binding of zinc ions, that there is no metallic taste observed; no localized activity and no observable efficacy in reducing the duration of common colds.

In as much as there is an important need to develop pleasant tasting lozenges and other means of introducing zinc ions to the oral and oral pharyngeal mucous membranes for the treatment of common colds; and in as much as serious mistakes taken from the prior art of taste management of zinc and other metallic ions have been made, particularly in the taste management of zinc lozenges; it is apparent that the errors of the prior art receive attention and a new way of eliminating the taste and aftertaste of ionizable zinc compounds be developed.

PRIMARY OBJECTIVE AND GENERAL DESCRIPTION OF INVENTION

Accordingly, it is a primary objective of this invention to disclose and claim a composition of matter that effectively masks the flavor and aftertaste of zinc gluconate and other ionizable compounds of zinc when such zinc compounds are intended to be absorbed into the oral and oral pharyngeal mucous membranes, and especially when such zinc compounds are intended for use in shortening the duration of common cold symptoms.

These primary objectives and other objects of this invention will be found apparent from the following general description and detailed examples.

According to the present invention, it has been unexpectedly and surprisingly found that ionizable zinc compounds such as zinc gluconate, zinc ascorbate and zinc acetate can be effectively and pleasantly flavor masked with anethole, (trans-Anethole; 1-Methoxy-4-(1-propenyl)benzene; p-Propenylanisole), to eliminate or greatly reduce the unpalatable taste and aftertaste of such zinc compounds.

Anethole, a highly stable oil, is the main constituent of essential oil of anise, star-anise and fennel. Anethole is almost totally insoluble in water and cannot chelate zinc ions. It has a sweet anise flavor and odor and is considered to be a flavor body or blender and has found use in alcoholic beverages, non-alcoholic beverages, frozen dairy desserts, baked goods, gelatins, puddings, meat and meat products, chewing gum, licorice candy, toothpaste, pharmaceuticals as a flavor and odor masking agent, and as a carminative, stimulant and expectorant in cough mixtures and lozenges and in fragrance compositions as a "sweetener".

Anise oil and other flavorings, but not anethole, are described in U.S. Pat. No. 4,469,674 for use as flavorings for stable oral compositions containing both zinc and floride compounds primarily intended to have anti-mouth odor and anti-caries activity. The amount of anethole contained in the anise oil in said previous invention is presented in amounts that include the amounts of anethole used in the present invention. The present invention differs by use of anethole which is only one of many distinct anise oil components. Anise oil contains 75 to 90% trans-anethole, estragole (methylchavicol); beta-caryophyllene; anise ketone (rho-methroxyphenylacetone); and other compounds in minor concentrations including anisaldehyde, anisic acid, linalool, limonene, alpha-pinene, acetaldehyde, rho-cresol, cresol, hydroguinone, beta-farnesene, gamma-himachalene and ar-curcumene. However there is no mention of the taste-masking effect of either anise oil or anethole on the zinc compounds in the previous invention; and similarly no mention of the effect of anise oil or anethole in masking the long-lasting after-taste of zinc compounds. The previous invention only mentions the use of anise oil as a flavoring for the composition which contains both zinc and floride compounds. The previous invention does not indicate if the zinc and floride composition had an objectionable taste or aftertaste in need of being flavor-masked. Said previous invention does describe a long-lasting effect of the composition on the level of volatile sulfur compounds, but with no parallel or similar mention of the effect of anise oil on the aftertaste of zinc compounds or of the zinc and floride composition.

The present invention differs from the previous invention in that only a component of oil of anise, anethole, is used only with a single component, zinc compounds, of the previously invented composition; and by the disclosure in the present invention that anethole, a single component of anise oil, is an effective flavor-mask and aftertaste mask for zinc compounds whereas anise oil is described in the previous invention as one of many possible flavorings with no distinction or preference between flavorings or distinction in relative flavor masking effectiveness between flavorings. Furthermore, the previous invention neither discerns between amounts of anise oil that effectively flavor the composition and those lower amounts that do not effectively flavor the composition, nor, does the previous invention discriminate between amounts of anise oil that effectively and ineffectively flavor-mask the taste and aftertaste of zinc; whereas the present invention clearly discloses and claims the range and near exact amounts or ratios of anethole needed to flavor-mask the taste and aftertaste of zinc. Finally, the present invention does not require any floride compounds, while the previous invention requires floride.

The present invention discloses that the taste-masking effect of anethole on zinc compounds is unexpectedly strong, surprisingly and unexplainably long-lasting and highly unique with no known parallel. Such parameter allows the sustained application of zinc gluconate and other ionizable zinc compounds in the form of a lozenge or by other similar means to the oral and oral pharyngeal mucosa with either no or reduced zinc taste or aftertaste. Such application can be at regular intervals, such as each two hours, and over a prolonged period, such as the course of a common cold with no or very little zinc taste or zinc aftertaste being present at any time. Such a special and unique property increases the utility of ionizable zinc compounds used in lozenges or otherwise in the treatment of the common cold. With the amount of high quality anethole properly balanced with zinc gluconate or other ionizable zinc compounds, it can completely mask the taste and aftertaste of zinc ions. A product containing both zinc and anethole can be so balanced that the taste of the product ranges from zinc-like to decidedly sweet and generally pleasant tasting. The amount of anethole can be varied so that the taste or aftertaste of zinc or anethole predominates.

In the case that a mildly objectionable zinc ion taste is desired, a lower ratio of anethole, about 30 to 40% the weight of zinc, may be used in the composition. Such action can be beneficial to reduce the possibility of accidental overdose of zinc. Conversely, it may be more desirable to use anethole at about 50 to 60 percent the weight of zinc to eliminate the taste of zinc and to prevent the aftertaste of zinc from emerging as the predominant taste hours later or overnight. Larger amounts of anethole in relation to zinc, such as a 60 to 100 percent ratio of anethole to elemental zinc, produce a stronger more dominant flavor of anethole. In small lozenges, such ratio may allow the taste of anethole to become particularly strong and perhaps objectionably strong. However, ratios of anethole to zinc can be substantially higher when the amount of zinc in a lozenge or other composition is small in comparison to the total amount of the composition.

The quality of anethole is an important factor in properly flavor-masking ionizable zinc compounds. Variations in commercially available anethole can account for significant differences in flavor-masking ability. Such variation was found in different batches from the same commercial source, and between different competing commercial sources. Therefore quality control of anethole is important to the final taste and sweetness of the composition herein disclosed. Anethole may be in liquid, spray dryed or microencapsulated form.

Although many other flavorings are insoluble, will not chelate zinc ions, and may be used to flavor zinc compound compositions, anethole is unique and exceptional in its ability to completely mask the taste and especially the aftertaste of ionizable zinc compounds. Such property of anethole was unexpected, unpredicted and previously undiscerned. Many zinc containing lozenges seen in the United States have been produced. None are known at this time to have used anethole as a sole flavor-masking agent. Although it has been used to mask the flavor of some pharmaceuticals for many years, there was no evidence found to suggest that it would have a long term effect in controling the significant, objectionable and long-lasting aftertaste of concentrated ionizable zinc compounds.

Other flavorings can be used with anethole to impart their own flavor including but not restricted to anise, eucalyptol, wintergreen, licorice, clove, cinnamon, spearmint, cherry, lemon, orange, lime, menthol, peppermint and various combinations, so long as they do not excessively chelate zinc ions, are pharmaceutically acceptable, are palatably and chemically compatible with anethole and the zinc compound being flavor-masked. In some cases, extra anethole is needed to compensate for the ability of other flavoring to unmask the taste and aftertaste of zinc.

The zinc and anethole combination may be used in conjunction with any base material as a carrier or binder that does not excessively chelate zinc ions; and in any form such as lozenges, soft candies, tablets, liquids, chewing gums, powders, sprays, and aerosols suitable for delivery of concentrated ionizable compounds of zinc to the oral and oral pharyngeal mucous membranes over a sustained period of time so as to permit a prolonged contact of ionizable zinc compounds in the mouth. The carrier may be sweet and may be sucrose, sucrose with dextrose, dextrose, fructose, or any other sweetener that does not excessively chelate zinc ions.

Mannitol, sorbitol and phenylalanine (in aspartame) and saccharin have been shown to have strong metal chelating properties. Mannitol and sorbitol are insufficiently sweet to justify their substitution for sugar or incorporation as an added sweetener although large amounts can eliminate the taste of zinc through chelation of zinc ions. Additionally, aspartame is not heat stable. In as much as saccharin is many hundreds of times sweeter than sugar, very small amounts of saccharin may be added to the composition to add extra sweetness. Consequently, to retain positively charge zinc and efficacy against common colds, mannitol, sorbitol, aspartame, and saccharin must not be added in chemically significant amounts.

As menthol-eucalyptol throat lozenges are an important and accepted treatment for sore throats and cough from common colds and allergies and since they make nasal passages feel clearer, it appears beneficial to expand the utility of such lozenges by the addition of soluble and ionizable zinc compounds. Therefore detailed descriptions of the effects of zinc gluconate flavor-masked with anethole in preparations containing menthol and eucalyptol are presented. However, it shall be readily understood that incorporation of menthol and eucalyptol have no significant effect on the zinc ion flavor-masking efficacy of anethole and that similar examples of zinc lozenges and other compositions flavor-masked with anethol but without menthol, eucalyptol or any other flavoring were demonstrated equivalent in flavor-masking ability to the examples shown herein with menthol or eucalyptol. It shall also be readily understood that the tastes, mouth feel and aromas of the compositions with menthol or eucalyptol differ from otherwise identical compositions without said flavorings.

The following examples will serve to illustrate, but not to limit, the present invention.

PREPARATION OF HARD CANDY STOCK

Laboratory scale batchs of hard candy were prepared under a strong vacuum. Mixtures of sucrose and fructose (at ratios varying from 2 to 1 to 3 to 1) and distilled water (20% weight of solids) were heated until they became clear at about 225° F. while stirring in an open 6-liter modified pressure cooker. The pressure cooker lid, modified with addition of a ⅜ diameter quick-release vacuum port, temperature and vacuum guages, was then fitted to the cooker. The pressure cooker, so modified to be a vacuum pan, was attached to a strong vacuum source with a one-half inch hose having a quick-release fitting. The temperature of the candy stock under a hard vacuum of 24 to 26 inches of vacuum first fell then rose sharply to 235° F. The vacuum pan was removed from heat at that temperature and detached from the vacuum source. The clear slightly tan liquid was poured into a lightly greased pan and cooled to room temperature where it was fractured into 150 to 200 gram pieces and stored in sealed containers.

Variations were made to include larger batchs, and batchs using glucose 42 DE or glucose 62 DE and sucrose and different ratios of ingredients. A surprising finding was that flavor-masked lozenges according to this invention using a sucrose/fructose base material were disproportionately better tasting than lozenges with a sucrose/glucose base material. Surprisingly, 1.8% elemental zinc, flavor-masked sucrose/glucose lozenges were flat and objectionable in taste and not significantly improved in taste over unflavored zinc gluconate lozenges. However, lower concentrations of zinc could be effectively flavor-masked using the sucrose/glucose base with little taste of anethole. Hard candy using either sucrose/fructose or sucrose/glucose were produceable at temperatures over 213° F. when the vacuum was held at about 25 inches.

COMPOSITIONS WITH A HARD CANDY BASE MATERIAL

The following examples comprise a hard candy base containing various amounts of elemental zinc per lozenge, with specific details listed for each example. The amount of zinc in each example is related to the amount of zinc in lozenges previously used to successfully treat common colds. For example 23 milligrams of zinc has been used to treat adults, while one-half that dose, 11.5 milligrams may be more useful to treat small children. Generally, 23 milligrams of zinc in these compositions resulted in 35 to 45 millimolar concentration in saliva and lozenges dissolved in saliva in 10 to 15 minutes. Taste tests of lozenges identical to the following examples but without anethole always resulted in a zinc taste and aftertaste, the severity of which depended upon dosage and the base material. Addition of about 5 milligrams of sodium saccharin to each 25 milligrams of zinc in each example was sufficient to significantly increase the overall sweetness of the compositions.

Example 1 - Preparation of Full-Strength Menthol-Eucalyptol Lozenges Containing Zinc Gluconate and Anethole About 200 grams of lozenge (troche, candy or tablet) ingredients was prepared to make one-hundred 1.26 gram hard candy lozenges with each lozenge containing 23 milligrams of elemental zinc as zinc gluconate. A batch consisted of 25.51 grams zinc gluconate, 1.82 grams anethole, 0.95 grams menthol, 0.48 grams eucalyptol and 171.10 grams hard candy base material. The menthol crystals were dissolved in the other flavor oils in a glass, not plastic, vial and were thoroughly mixed with granular zinc gluconate at room temperature. The hard candy stock was reheated to 230° F. and stirred to insure that all was completely liquified. The 100-lozenge mold was sprayed with PAM$^{tm}$ to prevent sticking and heated to about 250° F. The zinc gluconate and flavors were throughly but quickly mixed into the very viscous, dough-like, hard candy base at temperatures descending from 230° F. The dough-like mixture was spooned onto the mold, covered with a thin plastic sheet sprayed with PAM$^{tm}$, and pressed into the mold. The mold, its contents and plastic cover were quickly cooled to about 72° F., when the plastic sheet was removed and the excess lozenge ingredients were removed from the front face of the mold with a rotating blade. The mold was unscrewed from its back face and the 1.26 gram menthol-eucalyptol lozenges were gently pressed from the mold and glazed by reheating.

Each 1.26 gram lozenge theoretically contained 160.84 milligrams of zinc gluconate (equivalent to 23.00 milligrams elemental zinc), 11.50 milligrams anethole (equivalent to 50% of the elemental zinc), 6.00 mg menthol, and 3.00 mg eucalyptol. The lozenges contained about 1.8% elemental zinc. Taste tests indicated that the first note was that of anethole, quickly followed by strong menthol and eucalyptol taste and vapors in the nose. The taste and aroma were also described as ethereal, unusual, cold and pleasantly strong. No taste of zinc was present. There was no sour, salty, metallic or bitter taste of any kind noticed. The astringent mouth feeling normally associated with zinc gluconate lozenges was greatly attenuated. In excessively severe taste tests where such lozenges were dissolved in the mouth one after another (total about 600 mg zinc per day) as candy for 3 days, such action produced an ongoing enjoyable taste and nasal aromatic action and a barely detectable and unidentifiable early morning-overnight aftertaste. The unidentifiable aftertaste was mildly salty or salty-sweet, not unpleasant and different from that of zinc, anethole or normal early morning mouth-tastes.

Example 2 - Preparation of Children's Strength Menthol-Eucalyptol Lozenge Containing Zinc Gluconate and Anethole About 240 grams of lozenge ingredients was prepared to make one-hundred 1.26 gram hard candy lozenges with each lozenge theoretically containing 11.5 milligrams of elemental zinc as zinc gluconate. A batch consisted of 15.18 grams zinc gluconate, 1.09 grams anethole, 0.57 grams menthol, 0.28 grams eucalyptol, and 220.70 grams hard candy base material. The method of preparation was identical to that method described in example 1.

Each 1.26 gram lozenge theoretically had one-half the amount of zinc and flavoring as Example 1 and appeared otherwise identical to lozenges of Example 1. Taste tests showed they had a milder taste and were otherwise similar to the lozenges of Example 1.

Example 3 - Preparation of Double-Sized Menthol-Eucalyptol Lozenge Containing Zinc Gluconate and Anethole About 240 grams of lozenge ingredients was prepared to make fifty - 2.52 gram hard candy lozenges with each lozenge theoretically containing 23 milligrams of elemental zinc as zinc gluconate. A batch consisted of 15.18 grams zinc gluconate, 1.09 grams anethole, 0.57 grams menthol, 0.28 grams eucalyptol, and 220.70 grams hard candy base material. The method of preparation was identical to that method described in example 1.

Each 2.52 gram lozenge theoretically had the same amount of zinc and flavoring as Example 1 but had twice the amount of candy stock. Taste tests showed they were milder but otherwise similar in taste to the lozenges of Example 1.

Example 4 - Preparation of Double-Strength Menthol-Eucalyptol Lozenge Containing Zinc Gluconate and Anethole About 240 grams of lozenge ingredients was prepared to make fifty—2.52 gram hard candy lozenges with each lozenge theoretically containing 46 milligrams of elemental zinc as zinc gluconate. A batch consisted of 34.15 grams zinc gluconate, 2.44 grams anethole, 0.64 grams menthol, 0.32 grams eucalyptol, and 230.00 grams hard candy base material. The method of preparation was identical to that method described in example 1.

Each 2.52 gram lozenge theoretically had twice the amount of zinc flavoring and candy base material as Example 1. Taste tests showed they were identical in taste to the lozenges of Example 1.

Example 5 - Preparation of Quadruple-Sized Menthol-Eucalyptol Lozenge Containing Zinc Gluconate and Anethole About 240 grams of lozenge ingredients was prepared to make 25-5.04 gram hard candy lozenges with each lozenge theoretically containing 23 milligrams of elemental zinc as zinc gluconate. A batch consisted of 7.59 grams zinc gluconate, 0.54 grams anethole, 0.28 grams menthol, 0.14 grams eucalyptol, and 229.26 grams hard candy base material. The method of preparation was identical to that method described in example 1.

Each 5.04 gram lozenge theoretically had the same amount of zinc and flavoring as Example 1 but had quadruple the amount of candy stock. Taste tests showed they were milder but otherwise similar in taste to the lozenges of Example 1.

Example 6 - Preparation of Children's Strength Peppermint Lozenge Containing Zinc Gluconate and Anethole Having Zinc aftertaste About 200 grams of lozenge ingredients was prepared to make one-hundred 1.26 gram hard candy lozenges with each lozenge theoretically containing 10.0 milligrams of elemental zinc as zinc gluconate. A batch consisted of 11.21 grams zinc gluconate, 0.53 grams anethole, 1.0 gram peppermint oil and 189.0 grams hard-crack candy base material. The method of preparation was identical to that method described in example 1.

Each 1.26 gram lozenge theoretically had less than one-half the amount of zinc and one-sixth the amount of anethole compared to Example 1 which gave a ratio of anethole to zinc of about 31%. The lozenges were identical in appearance to lozenges of Example 1. Taste tests showed they had a mild pleasant anethole and peppermint taste but had a moderately objectionable zinc aftertaste which would preclude them from being assumed to be candy.

Example 7 - Preparation of Plain Lozenge Containing Zinc Gluconate and Anethole About 260 grams of lozenge ingredients was prepared to make one-hundred 1.26 gram hard candy lozenges with each lozenge theoretically containing 23 milligrams of elemental zinc as zinc gluconate. A batch consisted of 33.27 grams zinc gluconate and 2.38 grams anethole and 225 grams hard candy base material. The method of preparation was identical to that method described in example 1.

Each 1.26 gram lozenge theoretically had the same amount of zinc and anethole as Example 1 and appeared otherwise identical to lozenges of Example 1. Taste tests showed they had a sweet anethole taste with no taste or aftertaste of zinc. Extensive testing did not demonstrate any difference in flavor-masking from Example 1 and the absence of menthol and eucalyptol had no effect on flavor-masking zinc by anethole.

COMPOSITIONS WITH A POWDER AS A BASE MATERIAL

Example 8 - Preparation of Common Cold Powder Containing Zinc Gluconate and Anethole About 40 grams of powder was prepared to make 40 doses of one gram each with each theoretically containing 23 mg elemental zinc flavor-masked with 11.50 mg anethole (50% the amount of elemental zinc or 1% the amount of composition). A batch consisted of 6.74 grams zinc gluconate, 0.48 grams anethole and 34.75 grams of powdered confectioners sugar base material.

There was no taste or aftertaste of zinc in the white composition. The taste was also sweet and of anethole. There was no metallic, bitter, sour or salty taste to the composition. Added sugar produced ranges of zinc concentration from 23 milligrams per gram of composition to 23 milligrams of zinc per 200 grams of composition with similar but increasingly milder taste. Without anethole the taste and aftertaste of zinc in the powdered sugar material was strong and offensive.

COMPOSITIONS WITH A LIQUID AS A BASE MATERIAL

Example 9 - Preparation of Common Cold Mouth Wash and Gargle Liquid Containing Zinc Gluconate and Anethole About 310 grams of syrup was prepared to make 62 doses of 5 milliliter each with each dose theoretically containing 24.1 mg elemental zinc flavor-masked with 12.05 mg anethol. A batch consisted of 10.50 grams zinc gluconate, 0.75 grams anethole, 30 grams ethyl alcohol, 90 grams sucrose, 30 grams fructose, and 150 grams distilled water as a base material.

Sucrose and fructose were added to the water and boiled to liquify the mixture. Zinc gluconate was added and dissolved in the hot mixture. The anethole was mixed with alcohol. The clear zinc and syrup mixture and the clear anethol and alcohol mixture were mixed together where they formed a cloudy white suspension.

Taste tests with 5 milliler doses (theoretically 24.1 mg zinc) showed no evidence of a zinc taste or aftertaste. The syrup was sweet, with no bitter, salty, sour or metallic taste. The most prevalent taste was anethole. There was no astringent mouth feeling. Hours later or overnight after excessive use, the aftertaste was a barely detectable salty taste. Elemental zinc was 0.48% of the syrup composition and was 153 millimolar in concentration. The syrup was less than 10% alcohol. The syrup could be diluted with up to 500 milliliter water per 24.1 milligrams of zinc to achieve various concentrations ending at 1.53 millimolar concentration with no evidence of a zinc taste or de-emulsification of anethole at any concentration. An identical product without anethole had the strong and very objectionable taste and aftertaste of zinc and was highly astringent.

Example 10 - Preparation of Mouth Wash and Gargle Spray Containing Zinc Gluconate and Anethole The undiluted syrup of Example 7 was used as a spray mouth wash and gargle using a 625 milliliter per dose throat sprayer. Each dose theoretically gave 3 milligrams of elemental zinc. The taste and other results were identical to that of example 7.

Example 11 - Preparation of Mouth Wash and Gargle Aerosol Containing Zinc Gluconate and Anethole The syrup of Example 7 was used as a mouth wash or gargle aerosol using a pressurized aerosol dispenser. The dosage was entirely dependent upon the length of time that the valve was depressed. The taste and other results were identical to that of example 7. A strong zinc taste and aftertaste were noted without anethole.

COMPOSITIONS OF MASTICATIBLE SEMI-SOLIDS AS BASE MATERIAL

Example 12 - Preparation of Chewing Gum Containing Zinc Gluconate and Anethole About 145 grams of chewing gum ingredients was prepared to make thirty 4-gram chewing gum sticks with each stick theoretically containing 23 milligrams of elemental zinc as zinc gluconate. A batch consisted of 5.81 grams zinc gluconate, 0.42 grams anethole (50% of the amount of elemental zinc), and 138.60 grams of Wrigley's[R] Big Red cinnamon flavored chewing gum as base material. The chewing gum was softened to an easily workable consistency in a microwave oven. Premixed zinc and anethole were stirred into the chewing gum. The zinc-chewing gum composition was rolled into a 1/16 inch sheet and allowed to cool. There was no taste of zinc and the first and main flavor was of cinnamon followed by a slight anethole taste with no taste of zinc. An identical cinnamon gum with zinc but without anethole had the strong and objectionable taste and aftertaste of zinc and was much more astringent.

Example 13 - Preparation of Soft Candy Containing Zinc Gluconate and Anethole About 130 grams of gum drop candy ingredients was prepared to make twenty-five 4-gram gum drop candies with each gum drop theoretically containing 23 milligrams of elemental zinc as zinc gluconate. A batch consisted of 5.21 grams zinc gluconate, 0.37 grams anethole (50% of the amount of elemental zinc), and 124.0 grams of Brach's$^R$ Orange Slices gum drop candy as base material. The gum drop candy was softened in about one minute to an easily workable consistency in a microwave oven. Pre-mixed zinc and anethole were stirred into the gum drop candy. The composition was formed into a ½ inch sheet and allowed to cool and then cut into 4 gram pieces which were rolled in granulated sugar. The composition had no taste of zinc and the first and main flavor was of anethole followed by orange. There was no zinc aftertaste, but a slight salty aftertaste was observed. An identical gum drop with zinc but without anethole had the strong and objectionable taste and aftertaste of zinc and was astringent.

COMMENTS AND OTHER EXAMPLES

The preferred zinc compound for use in flavor-masked zinc compositions for oral application is zinc gluconate. The preferred method of applying zinc compounds to the oral mucosa is with lozenges. All ingredients to be used in compositions within the present invention are consumable or masticatable and are generally accepted as safe and approved for human consumption by appropriate authority.

Other compounds of zinc including zinc oxide, zinc tartarate, zinc aspartate, zinc citrate, zinc picolinate, zinc sulfate, zinc amino acid chelates, zinc orotate, zinc ascorbate, and zinc acetate were tested with anethole as a flavor-mask. The zinc taste of each was effectively flavor-masked by anethole. The extremely bitter taste of picolinate was difficult to mask. The astringency of zinc sulfate could be controlled with dilute formulations. Compounds of zinc including citrate, aspartate, tartarate, orotate and amino acid chelates were exceedingly simple to flavor-mask with anethole. Elimination of the taste of zinc in zinc acetate was no more difficult than for zinc gluconate and required the same amounts of anethole as did zinc gluconate.

The zinc lozenges, soft candies, powders, syrup, sprays and chewing gums described according to the present invention which include anethole have pleasantly sweet, non-metalic, non-sour, non-bitter, and non-salty tastes. The taste of zinc can be eliminated with an appropriate amount of high quality anethole which can be about 50 percent of the weight of zinc in the lozenge when freshly prepared but may be higher due to variations in the quality of anethole and other constituents of the composition. With or without a high gloss to the lozenges, after several weeks, a shift in taste towards a zinc taste may be observed as the flavor-mask mellows. Under those conditions flavors that appear in a given composition with anethole present at 55% to 60% the amount of zinc at the time of manufacture become more like the flavors that appear in a given composition with anethole present at 50% the amount of zinc on the day of lozenge manufacture. Therefore the amount of anethole in a composition may need adjustment to account for long-term shifts in flavor and the amount of anethole needed to mask the taste and aftertaste of zinc may be as high as 100% the amount of zinc in the composition.

Off-flavors, bitterness or zinc taste and aftertaste can also be caused by variations in the quality and condition of anethole. Only the highest quality anethole, preferably those with sufficient quality to be used in liqueurs should be used; as lower grades can have sharp or bitter tastes or may be poor flavor-masks for zinc and may require other taste modifiers, such as saccharin, to compensate for their off-flavor or bitterness. If lower quality anethole is used, ratios of the weight of anethole to the weight of zinc in any given composition can be increased to 100% the weight of zinc.

The oral side effects found in unformulated zinc gluconate are either absent or so greatly attenuated when properly flavor-masked with anethole in the present invention that they no longer appear significant. Taste-masking and side effect elimination is important in that zinc gluconate and other soluble and ionizable zinc compounds have been demonstrated useful in shortening the duration of common colds. Common colds often require oral zinc treatment about every two hours or so, and palatable compositions are needed as encouragement for a person in need of such treatment to continue treatment until symptoms are eliminated. The above examples serve to demonstrate that palatable zinc lozenges and other similar compositions are possible with anethole.

As will be apparent from the examples, the amount of zinc ion which will be released can be controlled by the amount or percentage of zinc compound incorporated in the base, and furthermore by its solubility and chemistry; although zinc gluconate appears to have near ideal chemical and physical properties. Also, as will be readily understood if a larger lozenge with a larger ratio of candy base to zinc and anethole is used that such is anticipated, and the time for complete dissolution can be slowed. It will be readily understood that large candies such as lollipops and all-day suckers up to 200 grams in size with varying amounts of zinc and anethole are anticipated. Using the above examples as guidelines, various lollipops having 23 to 200 milligrams of zinc similarly flavor-masked with anethole at about one-half the weight of zinc and weighing 50 grams, and all day-suckers having 23 to 200 milligrams of zinc similarly flavor-masked with anethole weighing 200 grams were prepared using large candy molds fitted with lollipop sticks as handles. Additionally, chewing gums and gum drops containing 23 to 50 milligrams of zinc similarly flavor-masked with anethole at about one-half the weight of zinc weighing up to 25 grams were prepared.

Also, as will be readily understood, if other release rates of zinc or other physical qualities are desired, a softer candy base or any other appropriate means of oral administration such as lozenges, candies, tablets, liquids, chewing gums, powders, sprays, and aerosols suitable for delivery of ionizable compounds of zinc to the oral and oral pharyngeal mucous membranes so as to permit a prolonged contact of zinc in the mouth may be used. The present invention provides new means of releasing zinc in the oral cavity, in various amounts, and at various rates determined by the formulation and composition used in a manner that is a substantial improvement over plain or otherwise flavored zinc compounds.

As will be apparent to one skilled in the art, variations can be made within the scope of the aforesaid description. Such variations being within the ability of one skilled in the art form a part of the present invention and are embraced by the following claims.

It is claimed:

1. Medicinal composition for release of zinc ions to the oral and oral pharyngeal mucous membranes of a human consisting essentially of suitable pharmaceutical carrier and uniformly contained in said pharmaceutical carrier;

anethole in an mount to flavor-mask the taste and aftertaste of zinc and;

an ionizable zinc compound;

wherein said zinc and anethole are slowly and uniformly released in the oral cavity as said composition is being orally consumed or masticated.

2. The composition of matter of claim 1 wherein said zinc compound is zinc gluconate and the amount of anethole is about 40 to about 100 percent that of ionizable zinc.

3. The composition of matter of claim 1 wherein said zinc compound is zinc acetate and the amount of anethole is about 40 to about 100 percent that of ionizable zinc.

4. The composition of matter of claim 1 wherein said zinc compound is zinc ascorbate and the amount of anethole is about 40 to about 100 percent that of ionizable zinc.

5. The composition of matter of claim 1 wherein the base material is a lozenge.

6. The composition of matter of claim 1 wherein the base material is fructose.

7. The composition of matter of claim 1 wherein the base material is a consumable powder.

8. The composition of matter of claim 1 wherein the base material is sugar.

9. The composition of matter of claim 1 wherein the means for releasing zinc is a consumable lozenge containing about 23 to 46 milligrams of zinc, as zinc gluconate, and 40 to 100 percent the weight of zinc as anethole in about 1 to about 200 grams of composition.

10. The composition of matter of claim 1 wherein the means for releasing zinc is a consumable powder containing about 23 to 46 milligrams of zinc, as zinc gluconate, and 40 to 100 percent the weight of zinc as anethole in about 1 to about 200 grams of composition.

* * * * *